United States Patent
Blaine et al.

(10) Patent No.: US 8,449,482 B2
(45) Date of Patent: May 28, 2013

(54) VIBRATING ANESTHESIA DEVICE

(75) Inventors: Robert C. Blaine, Buena Park, CA (US); Ashley S. Tilling, San Juan Capistrano, CA (US)

(73) Assignee: Blaine Laboratories, Inc., Santa Fe Springs, CA (US)

( * ) Notice: Subject to any disclaimer, the term of this patent is extended or adjusted under 35 U.S.C. 154(b) by 307 days.

(21) Appl. No.: 12/874,569

(22) Filed: Sep. 2, 2010

(65) Prior Publication Data

US 2011/0054386 A1    Mar. 3, 2011

Related U.S. Application Data

(60) Provisional application No. 61/239,484, filed on Sep. 3, 2009.

(51) Int. Cl.
*A61M 5/42* (2006.01)
*A61H 1/00* (2006.01)

(52) U.S. Cl.
USPC ............. 601/46; 604/22; 604/500; 601/15; 601/67; 601/72

(58) Field of Classification Search
USPC ............. 601/15, 18, 46, 57, 67–70, 72, 73, 601/78, 80, 84, 89, 93, 134, 139, 141, 142; 604/22, 500
See application file for complete search history.

(56) References Cited

U.S. PATENT DOCUMENTS

| | | | |
|---|---|---|---|
| 3,620,209 A * | 11/1971 | Kravitz | 601/79 |
| D331,288 S | 11/1992 | Yuen | |
| 5,160,194 A * | 11/1992 | Feldman | 362/109 |
| 5,171,225 A | 12/1992 | Sterrett | |
| D339,419 S | 9/1993 | Hood et al. | |
| D344,801 S | 3/1994 | Hughes et al. | |
| D360,036 S | 7/1995 | Doria | |
| D362,067 S | 9/1995 | Chang | |
| D374,932 S | 10/1996 | Engelman | |
| 5,626,628 A | 5/1997 | Ganansia | |
| 5,636,988 A * | 6/1997 | Murayama | 433/118 |
| 5,647,851 A | 7/1997 | Pokras | |

(Continued)

FOREIGN PATENT DOCUMENTS

| | | |
|---|---|---|
| WO | 9720588 A1 | 6/1997 |
| WO | WO 9720588 A1 * | 6/1997 |
| WO | WO 2006034324 A2 * | 3/2006 |
| WO | WO 2010110823 A1 * | 9/2010 |

OTHER PUBLICATIONS

"Adjacent." Dictionary.com.*

(Continued)

*Primary Examiner* — Clinton T Ostrup
*Assistant Examiner* — Eric Liu
(74) *Attorney, Agent, or Firm* — McKee, Voorhees & Sease, P.L.C.

(57) ABSTRACT

The hand-held vibration anesthesia tool of the present invention includes a housing in which a battery, vibratory motor, switch and light source are enclosed. A switch turns the motor and light on and off. A tip extends from the housing for touching a patient's skin. When the motor is actuated, vibrations are transmitted through the tip to the skin to create an anesthetized zone. The light defines a target for the needle or other treatment adjacent the tip.

18 Claims, 6 Drawing Sheets

U.S. PATENT DOCUMENTS

| | | | |
|---|---|---|---|
| 5,725,483 A * | 3/1998 | Podolsky | 601/15 |
| 5,925,002 A * | 7/1999 | Wollman | 601/70 |
| D438,979 S | 3/2001 | Gomes et al. | |
| 6,355,007 B1 * | 3/2002 | Zuckerbrod | 601/72 |
| 6,463,928 B1 | 10/2002 | Buisson | |
| 6,758,826 B2 * | 7/2004 | Luettgen et al. | 601/73 |
| D508,296 S | 8/2005 | Dibnah | |
| D558,396 S | 12/2007 | Sierra et al. | |
| 7,335,170 B2 * | 2/2008 | Milne et al. | 601/15 |
| D609,361 S | 2/2010 | McGarry et al. | |
| 7,699,794 B2 * | 4/2010 | Meyer et al. | 601/15 |
| 7,748,070 B2 | 7/2010 | Chan et al. | |
| 7,981,071 B2 * | 7/2011 | Goldberg | 604/22 |
| 2006/0074434 A1 * | 4/2006 | Wenstrom et al. | 606/96 |
| 2006/0178715 A1 * | 8/2006 | Ahn et al. | 607/96 |
| 2006/0253051 A1 | 11/2006 | Milne et al. | |
| 2007/0232967 A1 * | 10/2007 | Driscoll | 601/46 |
| 2008/0086063 A1 | 4/2008 | Baxter et al. | |
| 2008/0086159 A1 * | 4/2008 | Zweifler | 606/185 |
| 2008/0086187 A1 | 4/2008 | Baxter et al. | |
| 2008/0188779 A1 | 8/2008 | Vallero | |
| 2008/0255483 A1 | 10/2008 | Goldberg | |
| 2010/0179457 A1 * | 7/2010 | Blaine et al. | 601/46 |
| 2011/0054386 A1 | 3/2011 | Blaine et al. | |

OTHER PUBLICATIONS

Costlow, Tery, "DentalVibe Tricks Brain to Cut Pain", May 4, 2010, DesignNews.*

Stoecker, William V., et al., "Tripod vibration anesthesia", Dermatology Online Journal, vol. 14, No. 2, p. 1, 2008.

Smith, Kevin C., et al., "Vibration Anesthesia: A noninvasive method of reducing discomfort prior to dermatologic procedures", Dermatology Online Journal, vol. 10, No. 2, pp. 1-13, 2004.

Stoecker, William V. et al., "Tripod vibration anesthesia" Dermatology Online Journal, vol. 14, No. 2, p. 1, 2008.

Smith, Kevin C. et al., "Vibration Anesthesia: A noninvasive method of reducing discomfort prior to dermatologic procedures" Dermatology Online Journal, vol. 10, No. 2, p. 1-13, 2004.

* cited by examiner

VIBRATING ANESTHESIA DEVICE

CROSS-REFERENCE TO RELATED APPLICATIONS

This application claims priority under 35 U.S.C. §119 of a provisional application Ser. No. 61/239,484 filed Sep. 3, 2009, and which application is hereby incorporated by reference in its entirety.

FIELD OF THE INVENTION

The invention is directed toward a hand-held tool or device for providing an anesthetic effect on a patient via vibrations prior to a needle injection.

BACKGROUND OF THE INVENTION

Vibratory anesthesia is known in the medical industry as a method for temporarily numbing an area or zone on a patient prior to a medical procedure, such as an injection by a syringe. Vibration anesthesia is quick and easy, safe, highly effective, and inexpensive. The general concept behind such vibration anesthesia is the neuron transmitter depletion of alpha and C fibers of nerves which carry pain sensation. More particularly, according to one pain theory, certain nerve fibers which transmit information from vibration and touch receptors in the skin, stimulate inhibitory interneurons in the spinal cord, which in turn, act to reduce the amount of pain signal transmitted by alpha and C fibers from the skin to second-order neurons to cross the midline of the spinal cord and then ascend to the brain.

The anesthetic or analgesic effect of the vibrations minimizes pain in the patient undergoing an injection or other painful treatment. This vibration technique also calms patients who are needle-phobic. Vibratory anesthesia can also be used as a substitute for conventional injectable local anesthetics. In addition to the neurophysiological effect of vibration to reduce pain transmission, vibration may also have an additive placebo affect.

Cutaneous vibrators have also been used to relieve pain associated with a variety of dermatology procedures, including injections and laser treatments, for example, using a tripod muscle massager.

A primary objective of the present invention is the provision of a small device or tool which can be easily held in the hand for use by a medical professional, a relative or friend, or a patient to anesthetize a zone on the patient's skin prior to a procedure, such as an injection or drawing of blood.

Another objective of the present invention is the provision of a hand held device for vibration anesthesia which has a housing for the vibratory motor and battery, and a tip extending from the housing to transmit vibrations from the motor to the patient's skin.

Another objective of the present invention is the provision of a vibration anesthesia device having a tip which defines an anesthesia zone adjacent the vibrating tip.

A further objective of the present invention is the provision of a vibration anesthesia device having a tip which defines a treatment target between spaced apart points of the tip.

Yet another objective of the present invention is the provision of a vibration anesthesia tool having a light to illuminate a needle target adjacent the tip of the tool.

Still another objective of the present invention is the provision of a vibration anesthesia tool having an internal circuit board to control operation of the tool.

Another objective of the present invention is the provision of a vibration anesthesia device having a body with a triangular cross section for easy gripping between the thumb and one or two fingers of the user.

A further objective of the present invention is the provision of an anesthesia vibration device having a tip with a curved profile to define and partially surround the spot for a needle insertion.

Still another objective of the present invention is the provision of a method for minimizing pain for a needle insertion on a patient.

A further objective of the present invention is the provision of a vibration anesthesia device which is economical to manufacture, and which is safe, durable and effective in use.

These and other objectives will become apparent from the following description of the invention.

SUMMARY OF THE INVENTION

The vibration anesthesia tool of the present invention is designed to be hand held between a user's thumb and one or two fingers. The device or tool has a housing with a hollow body and a hollow head. A battery is mounted in the body, while a vibratory motor, circuit board are mounted in the head. A tip extends outwardly from the head portion of the housing and terminates in a curved edge or profile for engaging the skin. The curved profile of the tip defines an anesthesia zone within the profile and a needle insertion or treatment spot between the opposite end points on the curved end of the tip. The head of the housing also includes an LED to project a light beam onto the skin adjacent the tip so as to define and illuminate a treatment target, for example, the spot to insert the needle. The housing includes a switch to actuate the motor and light for use of the tool.

In use, an operator turns on the motor using the switch, and then touches the tip to the skin of the person receiving a shot or being treated at the treatment site. The motor vibrations are transmitted through the tip to the skin, so as to anesthetize the skin. The LED pinpoints the spot for the need insertion or other treatment.

DETAILED DESCRIPTION OF THE PREFERRED EMBODIMENT

Figure 1:
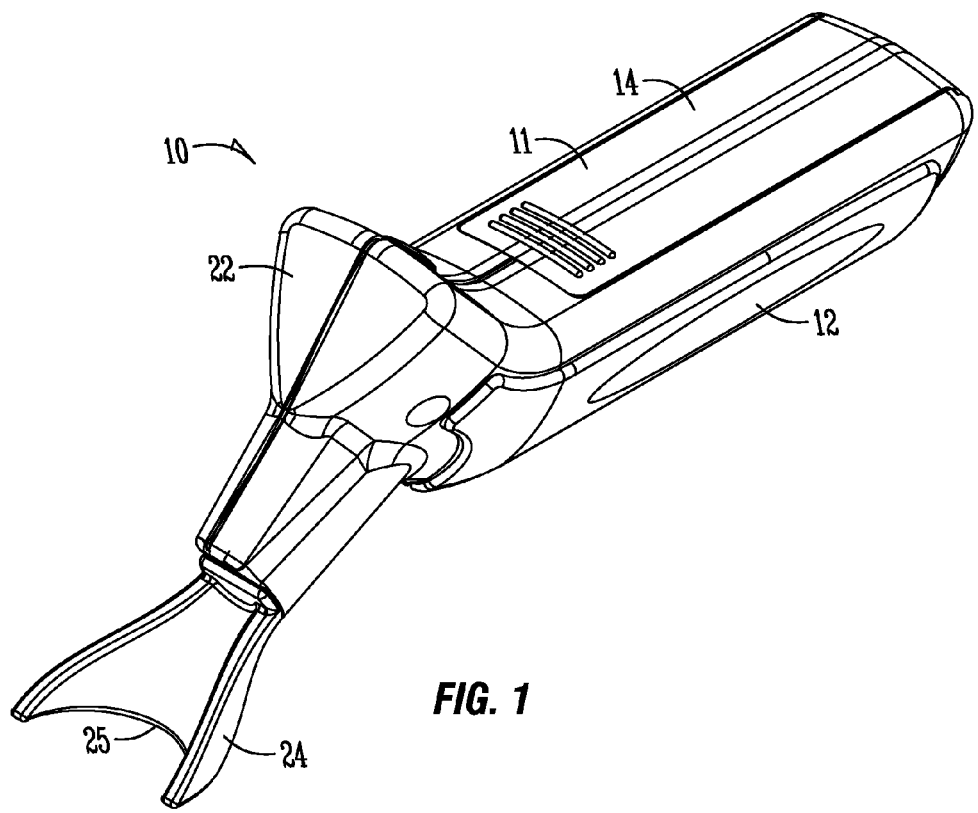
FIG. 1 is a front perspective view of the vibrating anesthesia device of the present invention.
Figure 2:
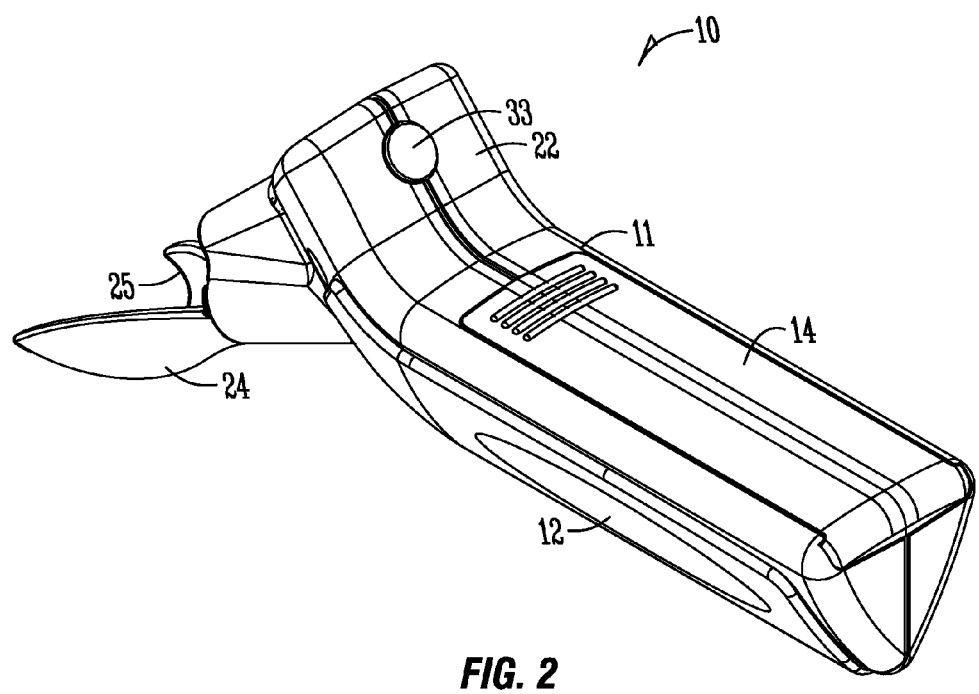
FIG. 2 is a rear perspective view of the device.
Figure 3:
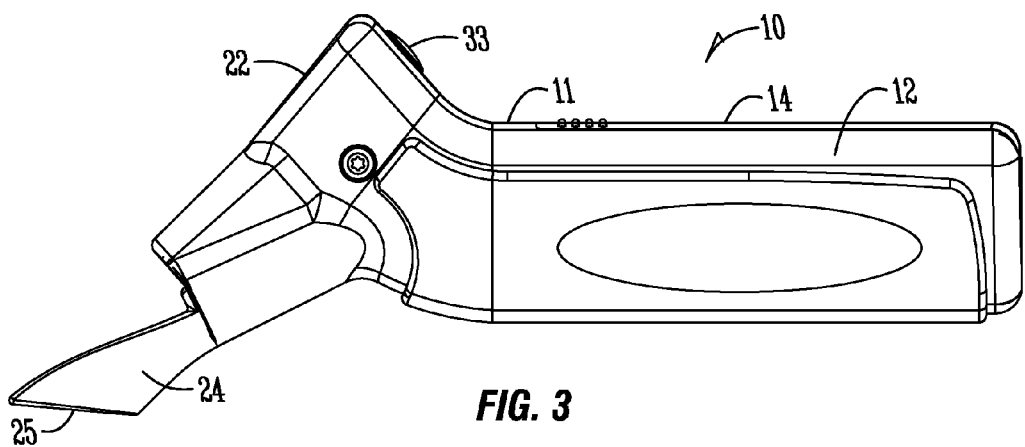
FIG. 3 is a left side elevation view of the device.
Figure 4:
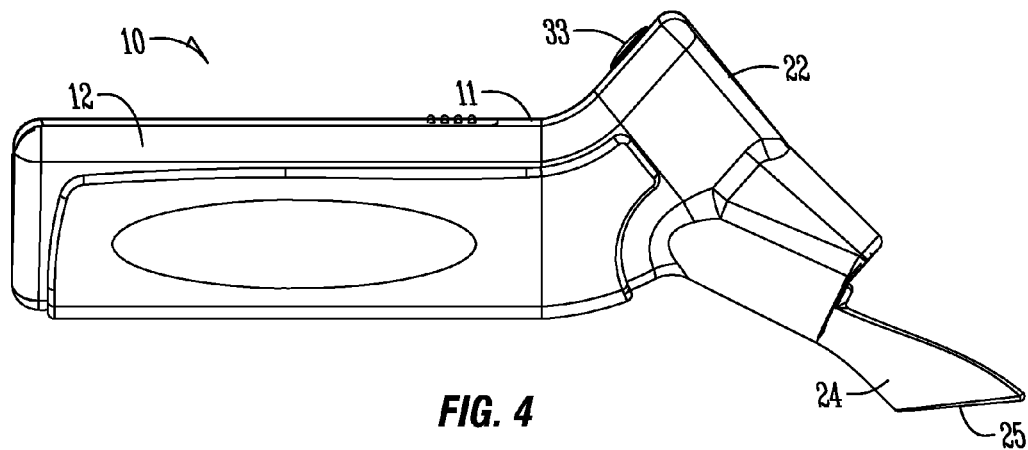
FIG. 4 is a right side elevation view of the device.
Figure 5:
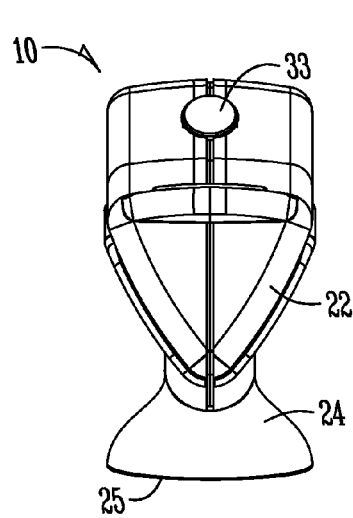
FIG. 5 is a rear end view of the device.
Figure 6:
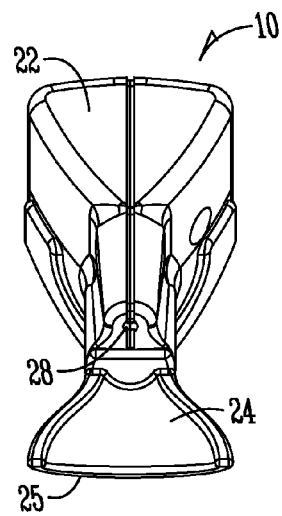
FIG. 6 is a front end view of the device.
Figure 7:
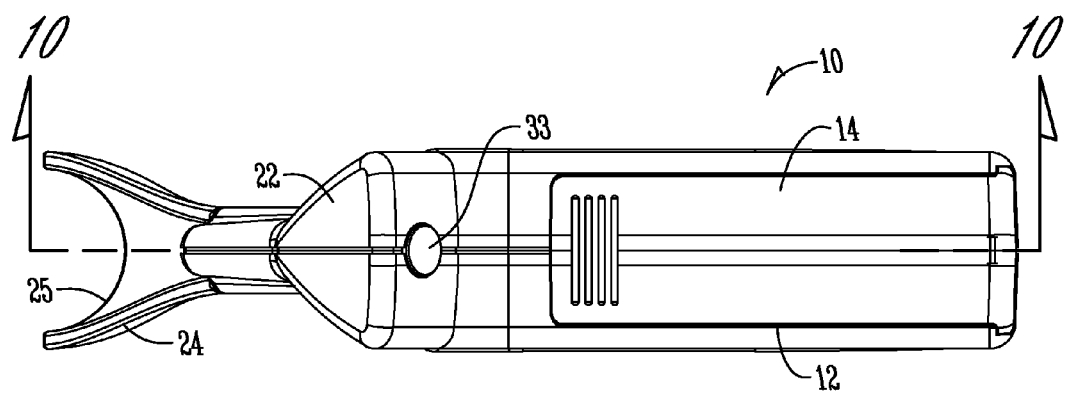
FIG. 7 is a top plan view of the device.
Figure 8:
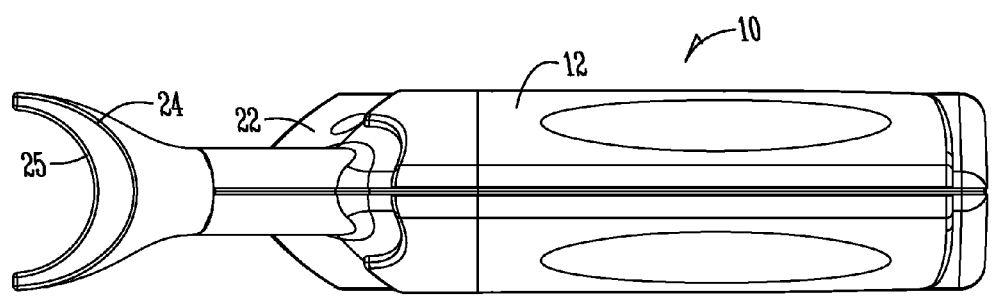
FIG. 8 is a bottom plan view of the device.

The hand-held tool or device 10 of the present invention is used for vibration anesthesia on a patient, such as a child, before they receive a syringe injection or other treatment which may cause pain to the patient. The tool 10 includes housing 11 with a hollow body 12 and a removable door or cover 14 to enclose a cavity which holds a battery 16. The cavity includes positive and negative terminals 18, 20 for engagement by the terminals of the battery 16. A spring 21 assures secure mounting of the battery 16 between the terminals 18, 20 and provides contact with the negative terminal 20.

Figure 9:
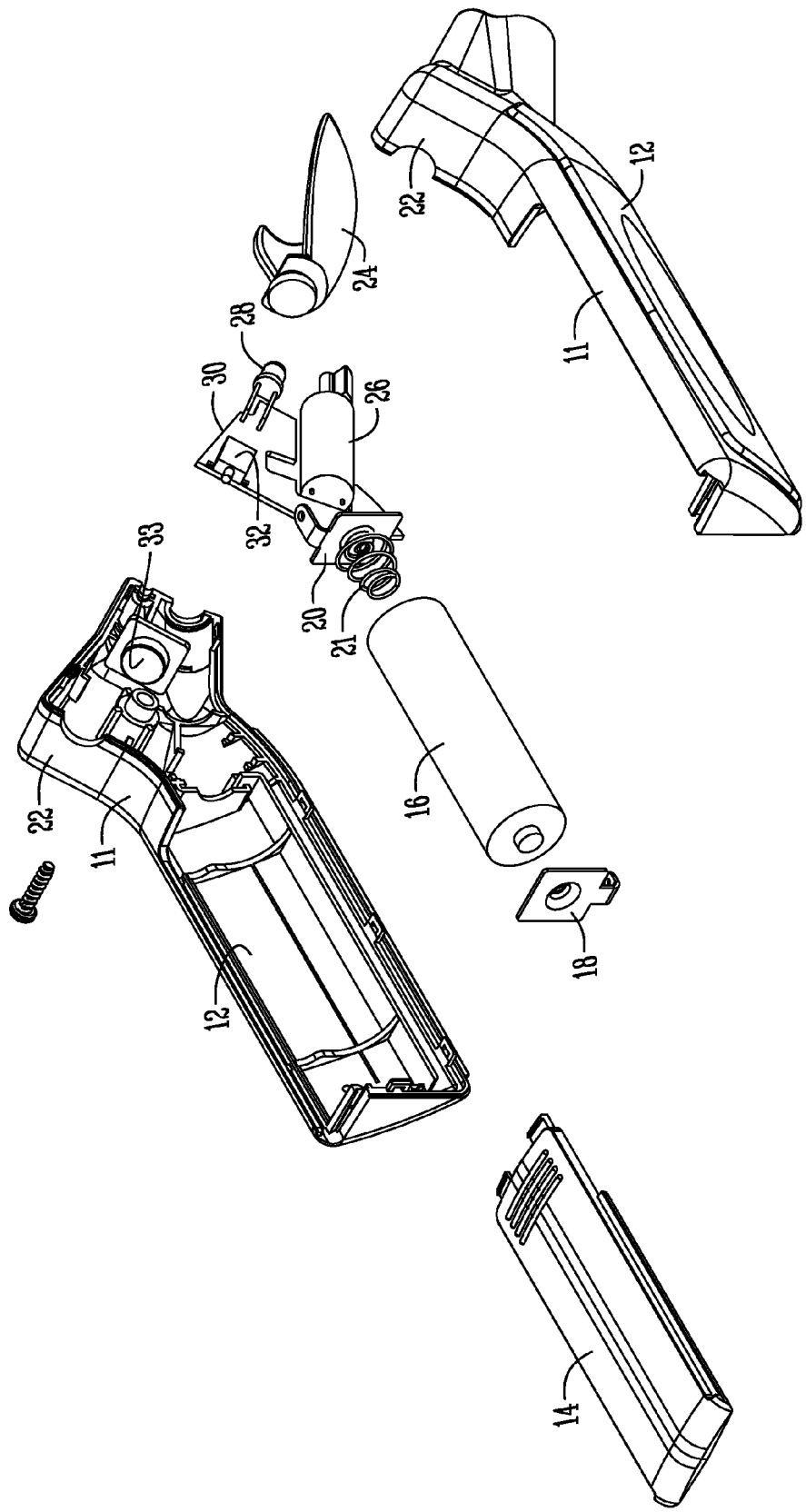
FIG. 9 is an exploded view showing the components of the vibration anesthesia tool of the present invention.
Figure 10:
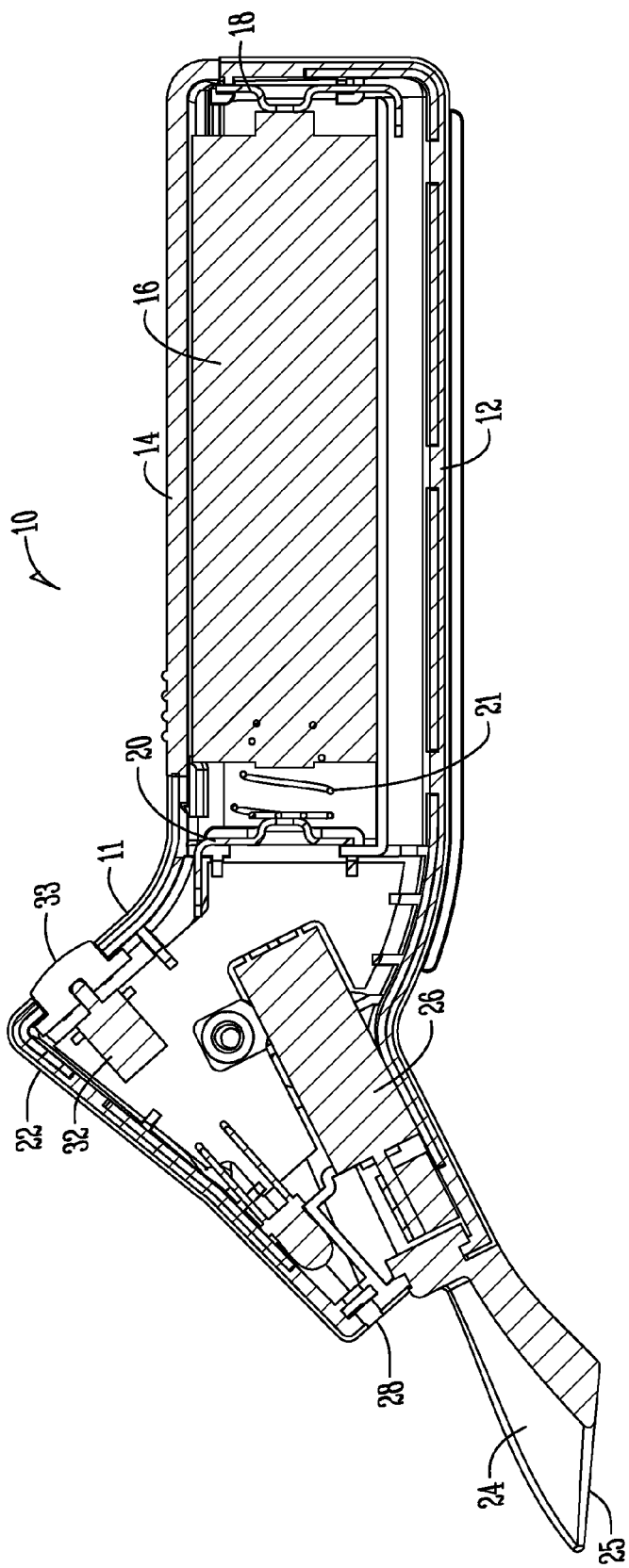
FIG. 10 is a sectional view of the tool taken along lines 10-10 of FIG. 7.

The tool housing 11 includes a hollow head 22 with a tip 24 extending forwardly from the head 22. The head 22 houses a small electric vibratory motor 26, a light source 28, such as an LED or laser marker, and a printed circuit board 30 which controls operation of the device 10. An on/off switch 32 with a push button control 33 is provided at the forward end of the body 12 for actuating the motor 26 and the light 28, both of which are in electrical connection to the battery 16 (though FIGS. 9 and 10 do not show the hard wire connections).

The motor 26, when turned on, imparts vibrations to the tip 24 of the tool 10. The tip 24 has a curved profile with a curved or semi-circular lower edge 25 so that the vibrations radiate inwardly from the curved tip, thereby defining an anesthesia zone within and adjacent the curved edge 25. The anesthesia zone may spread beyond the edge 25 of the tip 24 and the opposite end points of the edge 25. The light 28 provides a target for the syringe insertion or other treatment when the tool 10 is turned on. The switch 32 may have several settings to vary the speed of the motor 26, and thus the strength or intensity of the vibrations transferred to the patient's skin.

The body 12 of the device 10 has a triangular cross section, so it can easily picked up and held in a user's hand, between the thumb and one or two fingers, regardless of the size of the hand or other physical limitations, such as arthritis, deformities, or disabilities. It is understood that the shape of the tool may be varied from that shown in the drawings without departing from the scope of the invention.

Figure 11:
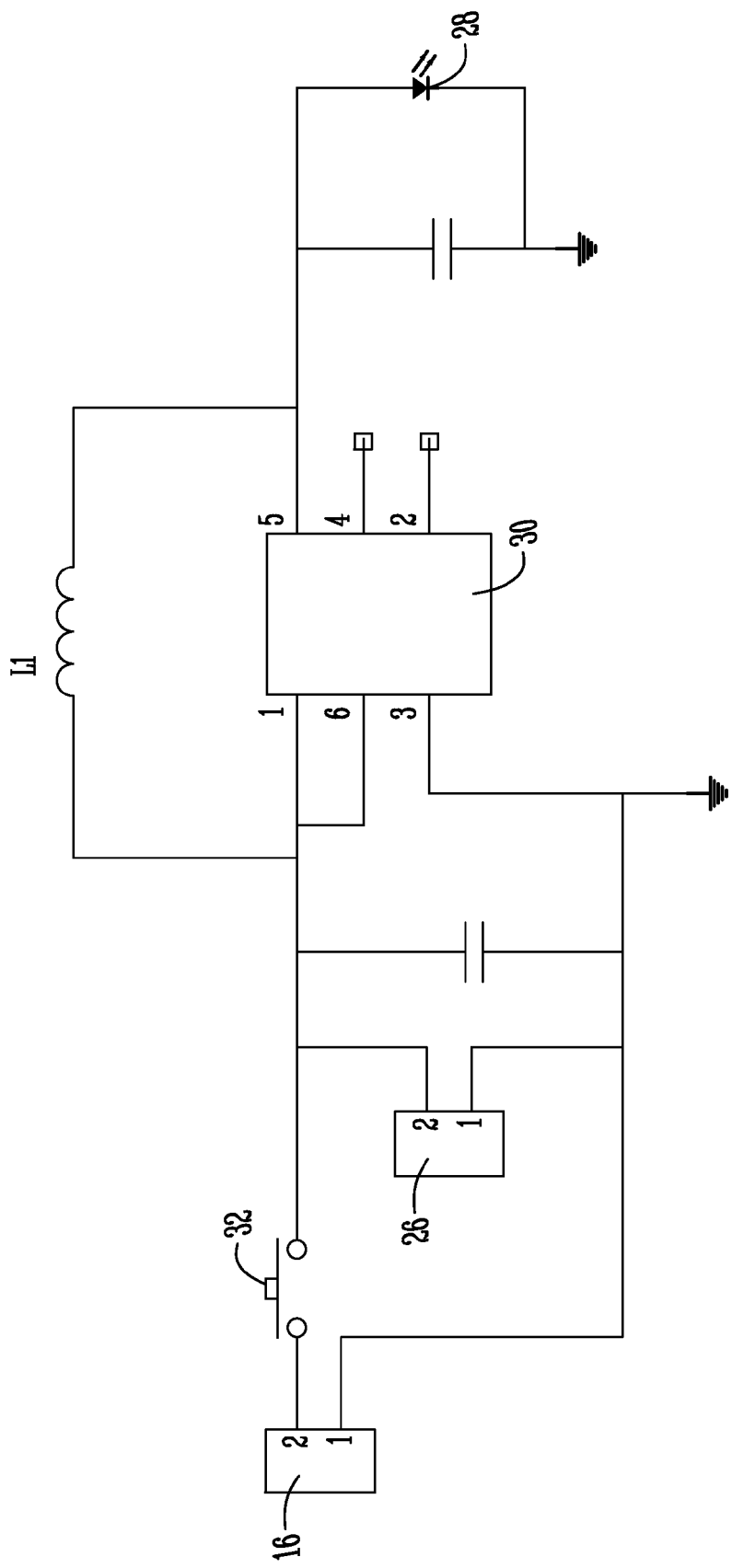
FIG. 11 is an electrical schematic for the components of the tool.

A preferred embodiment of the electrical circuitry for the device 10 is shown in FIG. 11. It is understood that the circuitry can take other configurations and may include other components to enhance or modify operation of the vibration anesthesia device 10. For example, the switch 32 may have a slide controller rather than a push button, and the motor 26 may have variable speeds.

In use, an operator touches or moves the switch so as to activate the motor 26, thereby generating vibrations which are transmitted through the tip 24. When the tip 24 touches the patient's skin, the vibrations create an anesthetic effect to numb the area adjacent the tip 24 of the tool 10. The light 28 identifies the preferred target within the anesthetized zone adjacent the tip edge 25 for a needle insertion or other treatment for the patient.

In a preferred embodiment of the device 10, the vibratory motor 26 has a vibration amplitude of approximately 1.8 g, and a frequency of approximately 120 Hz, with rpms between 9,000-11,000, and the electrical system has a nominal voltage of 1.5, a nominal current of approximately 450 mA (max) and a starting current of approximately 900 mA (max), with a terminal resistance of 1.8 ohm (max). The light 28 is preferably a packaged T-1 LED with a blue collar of 465 nm, and intensity of 700-1100 mcd (minimum), a voltage of 3.2, and a current of 20 mA. The switch 32 is preferably a momentary SMP tactile type switch with an actuation force of approximately 150 gf+/−10. Preferably, the battery 16 is a AA 1.5 V alkaline-type battery. It is understood that these preferred parameters may be modified without departing from the scope of the present invention.

The tool 10 eliminates or substantially reduces pain during a medical procedure, such as a shot. Such pain reduction or elimination is particularly useful in pediatrics, needle-phobic patients, and others who need numerous shots, such as diabetics receiving insulin shots on a daily or more frequent basis. The tool 10 can be used by a medical professional, including a doctor, a nurse, or a physician's assistant, by a relative or friend of the patient, or by the patient himself or herself who gives their own shots.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A hand-held tool for vibration anesthesia, comprising:
   a hollow body having opposite forward and rearward ends, and a hand-grip portion adapted to be held between the thumb and at least one finger during use of the tool;
   a battery operatively mounted in the body;
   a door removably mounted on the body to provide access to the battery;
   a hollow head at the forward end of the body and having opposite proximal and distal ends;
   an electric vibratory motor mounted in the head and electrically coupled to the battery;
   a switch on the body or the head to turn the motor on and off; and
   a tip having a proximal end extending into the head and a distal end extending forwardly from the head configured for transferring vibrations from the motor to an anesthesia zone on a person's skin when the tip touches the skin, thereby numbing the zone;
   the tip having a concave surface extending between the ends of the tip, the concave surface terminating in a C-shaped edge adapted to provide a continuous line of contact with the skin;
   the proximal end of the tip and the motor being adjacent one another inside the head;
   the anesthesia zone defining a target area configured to be positioned on the skin adjacent the C-shaped edge for a needle insertion;
   the tip having a longitudinal axis extending between the proximal and distal ends of the tip;
   the body having a longitudinal axis extending between the forward and rearward end of the body;
   the longitudinal axes of the tip and the body being non-parallel to one another;
   a substantially continuous line extending along a lower portion of the distal end of the head and extending along the proximal end of the tip to the distal end of the tip; and
   the tip having an increasing diameter from the proximal end of the tip to the distal end of the tip.

2. The tool of claim 1 further comprising a light source on the head to project light toward the anesthesia zone.

3. The tool of claim 1 further comprising a printed circuit board in the heal to control operation of the tool.

4. The tool of claim 1 wherein the body has a triangular cross section.

5. The tool of claim 1 wherein the head and body are angularly oriented with respect to one another.

6. The tool of claim 1 wherein the body has a longitudinal axis and the head extends angularly relative to the longitudinal axis.

7. The tool of claim 1 wherein the body has a longitudinal axis and the tip extends angularly relative to the axis.

8. The tool of claim 1 wherein the motor is positioned forwardly of the hand grip portion.

9. An improved vibrating anesthesia device, comprising:
   a housing having opposite proximal and distal ends;

a vibratory motor in the housing to generate vibrations;

a single tip extending from the distal end of the housing;

a switch on the housing to actuate the motor so as to transfer vibrations from the motor to the tip;

the tip having a proximal end and a distal end terminating in a forwardly facing C-shaped edge residing at an elevation lower than the entire housing when the housing is oriented horizontally for contacting the skin in a continuous line such that the vibrations are adapted to anesthetize the skin adjacent the C-shaped edge;

the housing and the tip forming a substantially flush surface extending along a lower portion of the distal end of the housing and extending along the proximal end of the tip to the distal end of the tip;

the tip tapering outwardly between the housing and the C-shaped edge; and the C-shaped edge defining an anesthesia zone configured to be positioned on the skin for a needle insertion.

10. The device of claim 9 further comprising a light source in the housing to illuminate the skin adjacent the tip edge.

11. The device of claim 9 further comprising an LED in the housing to project a light beam onto the skin to define a medical treatment target.

12. The device of claim 9 further comprising a circuit board in the housing to control operation of the device.

13. The device of claim 9 further comprising a battery in the housing to power the motor.

14. The device of claim 9 wherein the housing has a triangular body for gripping in a user's hand.

15. The device of claim 9 wherein the housing has a primary longitudinal axis and the tip extends angularly relative to the axis.

16. The device of claim 9 wherein the tip extends into the housing adjacent the motor.

17. The device of claim 9 wherein the housing has a handgrip portion and the motor is positioned between the handgrip portion and the tip.

18. The device of claim 17 wherein the tip has a rearward end extending into the housing adjacent the motor.

* * * * *